United States Patent [19]

Hamunen

[11] 4,422,974
[45] Dec. 27, 1983

[54] PROCESS FOR THE PURIFICATION OF β-SITOSTEROL ISOLATED FROM THE UNSAPONIFIABLES IN CRUDE SOAP FROM THE SULPHATE CELLULOSE PROCESS

[75] Inventor: Antti Hamunen, Lappeenranta, Finland

[73] Assignee: OY Kaukas AB, Finland

[21] Appl. No.: 396,335

[22] Filed: Jul. 8, 1982

[30] Foreign Application Priority Data

Jul. 21, 1981 [FI] Finland ................................. 812279

[51] Int. Cl.$^3$ .............................................. C07J 9/00
[52] U.S. Cl. .................................................. 260/397.25
[58] Field of Search ................................... 260/397.25

[56] References Cited

U.S. PATENT DOCUMENTS

| 4,044,031 | 8/1977 | Johansson et al. | 260/397.25 |
| 4,279,827 | 7/1981 | Ukkonen et al. | 260/397.25 |
| 4,298,539 | 11/1981 | Koskenniska | 260/397.25 |

Primary Examiner—Elbert L. Roberts
Attorney, Agent, or Firm—Scully, Scott, Murphy and Presser

[57] ABSTRACT

The invention relates to a process for the preparation of β-sitosterol having a low content of α-sitosterol of a sterol mixture isolated from the unsaponifiables obtained from crude soap from the sulphate cellulose process. The invention is based on crystallization of the sterol mixture from a mixture of an organic solvent and water, preferably 1,2-dichloroethylene or methyl ethyl ketone and water. By means of the process according to the invention, from starting materials containing 20 to 25% α-sitosterol is obtained a product which contains less than 5% α-sitosterol and which, when required, can be retreated by means of the process according to the invention to obtain β-sitosterol containing less than 1% α-sitosterol. When using methyl ethyl ketone as organic solvent, β-sitosterol is also purified of any betulin contained in the starting material.

4 Claims, No Drawings

PROCESS FOR THE PURIFICATION OF β-SITOSTEROL ISOLATED FROM THE UNSAPONIFIABLES IN CRUDE SOAP FROM THE SULPHATE CELLULOSE PROCESS

The present invention relates to a process for isolating β-sitosterol containing less than 5% α-sitosterol from a sterol mixture isolated from the unsaponifiables in crude soap from the sulphate cellulose process.

β-sitosterol is a compound which in the pharmaceutical industry can be used as raw material for steroid intermediates or also as such for pharmaceutical purposes.

β-sitosterol sources occurring in the nature comprise unsaponifiable fractions isolated from various vegetable materials, for example, the unsaponifiable substance of vegetable oils or sugar cane oil or the unsaponifiables of crude soap obtained from the sulphate cellulose process. However, sterol preparations isolated from these sources often contain as impurities undesired compounds and, accordingly, do not meet the rather strict quality requirements imposed by the pharmaceutical industry on β-sitosterol.

By means of the process according to the invention it is possible to prepare β-sitosterol in which the amount of impurities, especially α-sitosterol is small. The starting material in the process according to the invention is a sterol compound which is isolated from the unsaponifiable fraction, the so-called neutral substance extracted from crude soap obtained from the sulphate cellulose process using both softwood and hardwood, especially birch, as raw material and which, in addition, typically contains 65 to 70% β-sitosterol, 5% campesterol and 15 to 25% α-sitosterol. In addition, the sterol mixture may contain 0 to 10% betulin.

Some processes are available for the purification of sitosterol isolated from the neutral substance in sulphate soap.

In the Finnish Pat. No. 57 956 a sterol mixture containing α-sitosterol is treated with a strong acid, whereafter β-sitosterol is crystallized in a relatively pure form from organic solvents. The process suffers from the disadvantage that α-sitosterol which is useful for other than pharmaceutical purposes, for example, in the cosmetic industry, is destroyed.

The Finnish Pat. No. 58 333 describes a process in which α-sitosterol is removed from β-sitosterol concentrates by treating the concentrate with a solvent mixture containing aromatic and/or aliphatic hydrocarbons and esters and, in addition, possibly small amounts of ketones, alcohols, organic acids and water.

In the Finnish Published Specification No. 59 416 β-sitosterol is crystallized from a solvent mixture which contains xylene, toluene or mesitylene together with hexane or heptane, methanol, ethanol, acetone or methylene chloride and water.

The disadvantage in the two last-mentioned processes is the big number of solvent components which, in industrial applications, results in difficulties in the regeneration of solvent and the stabilization of the solvent composition. In addition—especially in solvents containing aliphatic hydrocarbons—any betulin contained in the starting sterol mixture will be concentrated in the β-sitosterol. The object of the present invention is to alleviate these disadvantages.

Characteristic to the invention is the following procedure: The α-sitosterol-containing sterol mixture used as starting material is dissolved while heating in a suitable solvent which may be methyl ethyl ketone, 1,2-dichloroethylene or ethyl acetate or a mixture thereof and an aliphatic or aromatic hydrocarbon, an amount of water is added that is >2% of the amount of organic solvent, and the purified sitosterol is precipitated by cooling the mixture to room temperature or below it while stirring. Alternatively, the water can be added to the mixture already during the dissolving step.

Thus, there are a large number of solvents and solvent mixture suitable for the above-mentioned purification procedure. In general, it can be said that a solvent-/solvent mixture in which water is dissolved to a limited extent can be used as organic solvent in said procedure. However, when aiming at a simple purification process it is preferred to use only one solvent instead of a solvent mixture. In particular, methyl ethyl ketone and ethylene dichloride have proved to be effective. When using methyl ethyl ketone, also any betulin contained in the starting sterol mixture will remain in the mother solution.

The examples in the following table will illustrate the invention in more detail.

The experiments of the table were carried out as follows:

10 g of a sterol mixture was dissolved in a mixture of an organic solvent and water while heating, the mixture was cooled to 20° C. while stirring whereafter sitosterol was filtered. In the experiments 8 to 11 the water was added only after sitosterol had been dissolved in the organic solvent.

TABLE

| Experiment | Impurities contained in the starting material | | Organic solvent | Solvent ml | Water ml | Yield of sitosterol g | Impurities contained in the product | |
|---|---|---|---|---|---|---|---|---|
| | α-sitost. | Betulin | | | | | α-sitosterol | Betulin |
| 1 | 17 | — | MEK | 100 | 6 | 5,5 | 4 | — |
| 2 | 17 | — | MEK | 100 | 12 | 5,5 | 2,4 | — |
| 3 | 17 | — | MEK | 80 | 10 | 6,1 | 4 | — |
| 4 | 17 | 5 | MEK | 100 | 12 | 5,5 | 2,5 | 0,8 |
| 5 | 6 | — | MEK | 100 | 10 | 7,2 | 0,6 | — |
| 6 | 25 | — | MEK | 100 | 10 | 4,7 | 5,5 | — |
| 7 | 25 | — | Ethylene dichloride | 100 | 10 | 6,0 | 3,4 | — |
| 8 | 22 | — | Ethyl acetate | 80 | 10 | 3,0 | 4,5 | — |
| 9 | 25 | — | Hexane-MEK 85:15 | 100 | 10 | 3,7 | 3,7 | — |
| 10 | 20 | — | Hexane-ethyl acetate 85:15 | 100 | 10 | 4,2 | 2,9 | — |
| 11 | 22 | 2 | Hexane-ethyl acetate 85:15 | 100 | 10 | 4,0 | 3,1 | 3,0 |
| 12 | 22 | — | Hexane-xylene: | 100 | 10 | 3,8 | 3,8 | — |

TABLE-continued

| Experiment | Impurities contained in the starting material | | Organic solvent | Solvent ml | Water ml | Yield of sitosterol g | Impurities contained in the product | |
|---|---|---|---|---|---|---|---|---|
| | α-sitost. | Betulin | | | | | α-sitosterol | Betulin |
| | | | ethyl acetate | | | | | |

By repeating the purification procedure, a product having an α-sitosterol content of less than 1% is obtained with the sitosterol obtained from the purification treatment.

What I claim is:

1. A process for isolating beta-sitosterol containing less than 5% alpha-sitosterol from a sterol mixture isolated from the unsaponifiables in crude soap derived from the sulphate cellulose process, comprising:
   (a) adding to the sterol mixture one organic solvent and water, said organic solvent selected from the group consisting of 1,2-dichloroethylene, methyl ethyl ketone and ethyl acetate, the sterol mixture and the organic solvent having a weight ratio between about 1:3 and about 1:20, and wherein the amount of water is greater than 2% of the organic solvent,
   (b) heating the admixture obtained from step (a) until the sterol mixture is dissolved,
   (c) precipitating a product rich in beta-sitosterol by cooling the admixture to at least room temperature, and
   (d) separating the precipitated product rich in beta-sitosterol from the solution by filtration.

2. A process for isolating beta-sitosterol containing less than 5% alpha-sitosterol and less than 1% betulin from a sterol mixture isolated from the neutral substance in crude soap containing 1 to 20% betulin, comprising:
   (a) adding to the sterol mixture methyl ethyl ketone and water, the sterol mixture and the methyl ethyl ketone having a weight ratio between about 1:3 and about 1:20, and wherein the amount of water is greater than 2% of the organic solvent,
   (b) heating the admixture obtained from step (a) until the sterol mixture is dissolved,
   (c) precipitating a product rich in beta-sitosterol by cooling the admixture to at least room temperature, and
   (d) separating the precipitated product rich in beta-sitosterol from the solution by filtration.

3. The process of claim 1 wherein the sterol mixture and the organic solvent have a weight ratio of between about 1:7 and about 1:10.

4. The process of claim 2 wherein the sterol mixture and the methyl ethyl ketone have a weight ratio of between about 1:7 and about 1:10.

* * * * *